United States Patent [19]

Berguer et al.

[11] Patent Number: 5,100,422

[45] Date of Patent: Mar. 31, 1992

[54] BLOOD VESSEL PATCH

[75] Inventors: Ramon Berguer, West Bloomfield, Mich.; Robert C. Farnan, Tucson, Ariz.; William M. Colone, Phoenix, Ariz.; Rajagopal R. Kowligi, Tempe, Ariz.; Linda V. Della Corna, Glendale, Ariz.; Joseph B. Sinnott, Mesa, Ariz.

[73] Assignee: Impra, Inc., Tempe, Ariz.

[21] Appl. No.: 358,785

[22] Filed: May 26, 1989

[51] Int. Cl.⁵ .................. A61B 17/00; A61F 2/06; F16B 21/00; A61L 15/00
[52] U.S. Cl. .................................. 606/151; 623/1; 411/339; 602/46
[58] Field of Search .................. 623/1, 11, 12; 428/304.4, 308.4, 322.2, 207.0, 339, 411.1, 339; 128/155, 156; 606/151

[56] References Cited

U.S. PATENT DOCUMENTS

| Re. 31,618 | 7/1984 | Mano et al. | 3/1.4 |
|---|---|---|---|
| 3,279,996 | 10/1966 | Long et al. | 167/82 |
| 3,479,670 | 11/1969 | Medell | 3/1 |
| 3,585,647 | 6/1971 | Gajewski et al. | 3/1 |
| 4,011,861 | 3/1977 | Enger | 128/2.06 |
| 4,173,689 | 11/1979 | Lyman et al. | 521/64 |
| 4,187,390 | 2/1980 | Gore | 7/18 |
| 4,193,138 | 3/1980 | Okita | 3/1.4 |
| 4,194,041 | 3/1980 | Gore et al. | 428/315 |
| 4,208,745 | 5/1980 | Okita | 3/1.4 |
| 4,304,010 | 12/1981 | Mano | 3/1.4 |
| 4,306,318 | 12/1981 | Mano et al. | 3/1.4 |
| 4,321,711 | 3/1982 | Mano | 3/1.4 |
| 4,344,999 | 8/1982 | Gohlke | 428/212 |
| 4,355,426 | 10/1982 | MacGregor | 3/1.4 |
| 4,377,010 | 4/1983 | Fydelor et al. | 3/1.4 |
| 4,441,215 | 4/1984 | Kaster | 3/1.4 |
| 4,586,504 | 5/1986 | de Medinaceli | 606/152 |
| 4,657,544 | 4/1987 | Pinchuk | 623/1 |
| 4,718,907 | 1/1988 | Karwoski et al. | 623/12 |
| 4,743,258 | 5/1988 | Idaka et al. | 623/1 |
| 4,829,993 | 5/1989 | Silvey | 128/155 |

FOREIGN PATENT DOCUMENTS 0157178 10/1985 European Pat. Off. .
2077107A 12/1981 United Kingdom .

OTHER PUBLICATIONS

*An In Vitro Study of the Properties Influencing Staphylococcus Epidermidis Adhesion to Prosthetic Vascular Graft Materials,* Joel M. Harris, M.D., and Louis F. Martin, M.D., Ann. Surg., Nov., 1987, pp. 612-619.

Promotional Literature for "Tecoflex" by Thermedics, Inc., Tecoflex Solution Processible Grades, 470 Wildwood Street, Woburn, Mass.

Kenney et al., "Evaluation of Compliant and Noncompliant PTFE Vascular Prostheses", *Trans. Am. Soc. Artif. Intern. Organs,* vol. XXXIV, 1988, pp. 661-663.

"The Role of Patch Angioplasty After Carotid Endarterectomy", Imparato, Journal of Vascular Surgery, vol. 7, No. 5, May, 1988, pp. 715-716.

Shu et al., "Flow Phenomena in Compliant and Noncompliant Arterioenous Grafts", *Trans. Am. Soc. Artif. Intern. Organs,* vol. XXXIV, 1988, pp. 519-523.

Salvian, A., Baker, J. D., Machleder, H. I., Busuttil, R. W., Barker, W. F., Moore, W. S., Cause and Noninvasive Detection of Restenosis After Carotid Endarterectomy, Am. J. Surg., 1983; 146:29.

Keagy, B. A., Edrington, R. D., Poole, M. A., Johnson, G., Incidence of Recurrent or Residual Stenosis After Carotid Endarterectomy, Amer. J. Surg., 1985; 149:722-4.

Hertezr, N. R., Beven, E. G., O'Hara, P. J., Krajewski, L. P., A Prospective Study of Vein Patch Angioplasty During Carotid Endarterectomy, Ann. Surg., 1987; 5:628-35.

Archie, J. P., Prevention of Early Restenosis and Thrombosis-Occlusion After Carotid Endarterectomy by Saphenous Vein Patch Angioplasty, Stroke 1986; 17:901-4.

Deriu, G. P., Ballotta, E., Bonavina, L., Grego, F., Alvino, S., Franceschi, L., Meneghetti, G., Saia, A., The Rationale for Patch-Graft Angioplasty After Carotid Endarterectomy: Early and Long-Term Follow-Up, Stroke 1984; 15:972-9.

Eikelboom, B. C., Ackerstaff, R. G. A., Hoeneveld, H., Ludwig, J. W., Teeuwen, C., Vermeulen, F. E. E., Welten, R. J. T., Benefits of Carotid Patching: A Randomized Study, J. Vasc. Surg., 1988; 7:240-7.

Schultz, G. A., Zammit, M., Sauvage, L. R., Spender, M. P., Kowalsky, T. E., Goff, S. G., Smith, J. C., Carotid Artery Dacron Patch Angioplasty: A Ten-Year Experience, J. Vasc. Surg., 1987; 5:475-8.

Carney, W. I., Lilly, M. P., Intraoperative Evaluation of PTFE, Darcon and Autogenous Vein as Carotid Patch Materials, Ann. Vasc. Surg., 1987; 538-6.

Akkerman et al., *Thrombosis and Atherosclerosis, IV Treatment*, 1984, Boehringer Ingelheim International GmbH, pp. 385-393.

"The GORE-TEX Cardiovascular Patch", advertisement by W. L. Gore & Associates, Inc., copyright 1989.

"MEADOX Cardiovascular Fabrics", advertisement (initial date of publication unknown).

Ott et al., "Carotid Endarterectomy without Temporary Intraluminal Shunt", Ann. Surg., Jun. 1980, vol. 191, No. 6, pp. 708-714.

Deriu et al., "The P.T.F.E. Graft Angioplasty After Endarterectomy. Personal Experience and Longterm Follow-Up", Vascular Surgery, Jan.-Feb. 1984, vol. 18, No. 1, pp. 37-41.

*Primary Examiner*—Stephen C. Pellegrino
*Assistant Examiner*—Gary Jackson
*Attorney, Agent, or Firm*—Cahill, Sutton & Thomas

[57] ABSTRACT

A vascular patch for closing an incision in a blood vessel includes a base layer of expanded polytetrafluoroethylene (PTFE) having an outer coating of an elastomeric, biocompatible material such as polyurethane to minimize suture hole bleeding. Suture guidelines are formed upon the ablumenal side of the PFTE base layer prior to application of the elastomeric coating to facilitate proper and consistent placement of sutures. A colorant is added to the elastomeric coating to identify the ablumenal side of the vascular patch. The vascular patch is made by mounting an expanded PTFE tube upon a mandrel and applying a water based PFTE ink as a helical stripe about the outer surface of the PTFE tube to form the suture guidelines. The striped PTFE tube is then dip-coated or spray-coated with the elastomeric coating to which the colorant has been added. The PTFE tube is slit to form a flat sheet from which vascular patches are cut.

11 Claims, 2 Drawing Sheets

BLOOD VESSEL PATCH

CROSS-REFERENCE TO RELATED PATENT APPLICATIONS

1. "LONGITUDINALLY COMPLIANT PTFE GRAFT", Ser. No. 358,787, filed concurrently herewith, naming Della Corna et al. as inventors, and assigned to the assignee of the present invention, now issued as U.S. Pat. No. 4,955,899.

2. "NON-POROUS COATED PTFE GRAFT", Ser. No. 358,011, filed concurrently herewith, naming Kowligi et al. as inventors, and assigned to the assignee of the present invention.

BACKGROUND OF THE INVENTION

1. Field of the Invention

The present invention relates generally to vascular patches used to close an incision in a blood vessel, and more particularly, to a prosthetic vascular patch using an expanded, porous polytetrafluroethylene (PTFE) base layer having an outer elastomeric coating to reduce suture hole bleeding; the present invention also relates to methods for manufacturing such vascular patches.

2. Description of the Prior Art

A number of surgical operations require that an incision be formed in the wall of a blood vessel. Such surgical operations include thrombectomies, endarterectomies, and aneurysmal repair procedures. Carotid endarterectomy is believed to be the most common vascular procedure performed today in the United States. Other surgical procedures which often require that incisions be formed in the wall of a blood vessel include inter-aortic balloon pump procedures, laser procedures, and operations to remove anastomotic hyperplasia.

Currently, there are three techniques used to close the incision in a blood vessel following the completion of one of the above-listed surgical operations. One of these closure techniques is known as a primary closure or simple closure, wherein the incision in the blood vessel is sewn together without the use of a patch. A second technique used to close the incision in a blood vessel uses a section from another vessel, such as a portion of the saphenous vein, as a patch over the incision. The third technique uses a prosthetic material as a patch for closing the wound. The use of a blood vessel patch in conjunction with carotid endarterectomy procedures is generally described by Imparato, *Journal of Vascular Surgery*, Volume 7, No. 5, May 1988, pages 715–716.

Regardless of which of the three closure techniques described above is used, a wound is produced in the vessel which typically results in some thickening of the blood vessel wall when the vessel heals. When the primary closure, or simple closure, technique is used to close the incision, the vessel typically has a reduced diameter at the entry site following surgery as compared with the original diameter of the vessel at the entry site. Some studies have reported that the use of the primary closure technique is subject to the problem of recurrent stenosis at the location where surgical intervention was required, possibly due to the narrowing of the vessel accompanied by thickening of the vessel wall at the entry site. By using a patch, the vessel has a greater diameter at the entry site as compared with the use of the primary closure technique, and accordingly, thickening of the vessel wall at the entry site is less significant.

Patches taken from a section of another vessel in the body provide the advantage of widening the vessel at the entry site where surgical intervention was required, while presenting a natural surface to the blood carried by the vessel. A natural, or autogenous, patch, such as a patch formed from a section of the saphenous vein, has a live intimal surface that reduces thrombogenicity; such a natural patch also has a functional vascular system which reduces healing time. However, this technique requires that an additional surgical operation be performed, namely obtaining a section of the saphenous vein. Such saphenous vein patches are typically taken from above the ankle to below the groin regions. Frequently, no acceptable vein for creating a patch is available. In addition, natural patches have been reported to dilate or rupture if the vessel used to make the patch is not sufficiently strong.

The use of a prosthetic patch avoids the disadvantage of performing a second surgical operation to harvest a natural patch from another vessel in the body. Moreover, prosthetic patches have sufficient strength to avoid the dilation and rupturing problems associated with natural patches. The synthetic materials most commonly used to form prosthetic patches are Dacron cloth and PTFE. Dacron-based patches are sufficiently porous that they must first be preclotted with the patient's blood to prevent leakage through the patch following implantation. On the other hand, PTFE patches do not require any preclotting prior to implantation. Moreover, PTFE patches are generally softer and easier to handle than Dacron patches. Moreover, the PTFE surface is less thrombogenic than the preclotted Dacron surface, and PTFE patches have minimal aneurysmal complications as compared with those associated with Dacron patches.

The principal disadvantage of prosthetic PTFE patches, as compared with natural patches or Dacron patches, is the tendency of such PTFE patches to leak blood from the suture holes after the patch is sewn to the wall of the blood vessel. Such suture hole bleeding results in substantial blood loss, a prolongation of the surgical operation time, and occasionally the need for a blood transfusion.

Attempts to diminish bleeding from arterial PTFE patches have included the temporary use of collagen-derived sheets, collagen powders, and oxycellulose compounds applied over the suture line. However, no satisfactory decrease in the amount of bleeding has been achieved using these methods. A more effective, though still not satisfactory, manner of sealing the patch suture line is the use of human cryoprecipitate activated with a mixture of a calcium and thrombin. This involves the risk inherent to the administration of blood products from human sources; in addition, this compound is relatively expensive.

Accordingly, it is an object of the present invention to provide a synthetic vascular patch for closing incisions formed in the walls of blood vessels and which minimizes suture hole bleeding associated with current PTFE vascular patches.

It is another object of the present invention to provide such a vascular patch which avoids the requirement for preclotting the patch with the patient's blood.

It is still another object of the present invention to provide such a vascular patch which is biocompatible, which has minimal thrombogenicity, which is physically strong, and which heals relatively quickly.

It is a further object of the present invention to provide such a vascular patch which facilitates the proper and consistent placement of sutures used to secure the vascular patch to the blood vessel in which an incision has been made.

It is a still further object of the present invention to provide such a vascular patch wherein the lumenal surface of the patch that is to be placed against the blood vessel wall is readily discernable from the ablumenal surface of such patch.

It is an additional object of the present invention to provide a method for efficiently and economically manufacturing such blood vessel patches.

These and other objects of the present invention will become more apparent to those skilled in the art as the description thereof proceeds.

SUMMARY OF THE INVENTION

Briefly described, and in accordance with a preferred embodiment thereof, the present invention relates to an improved vascular patch for closing incisions formed in blood vessels and includes a sheet or layer of expanded porous PTFE material having a first lumenal side adapted to overlie the blood vessel, and having a second opposing ablumenal side adapted to face away from the blood vessel. A layer of an elastomeric coating is applied over at least the peripheral portions of the ablumenal side of the PTFE layer to minimize bleeding at suture holes formed within such peripheral portions of the vascular patch. The lumenal side of the PTFE layer is left uncoated to permit the porous expanded PTFE surface to be in direct contact with the blood.

The elastomeric coating applied to the ablumenal side of the PTFE layer is preferably polyurethane but may generally be selected from the group of elastomers consisting of medical-grade silicone rubber elastomers, segmented polyurethanes, polyurethane-ureas, and silicone-polyurethane copolymers. Preferably, a colorant is incorporated within the elastomeric coating to distinguish the uncoated lumenal side of the PTFE layer from the coated ablumenal side of the PTFE layer.

Indicia may also be formed upon the ablumenal side of the PTFE layer beneath the elastomeric coating applied thereto. Such indicia are visible through the elastomeric coating and help distinguish the uncoated lumenal side of the PTFE layer from the coated ablumenal side of the PTFE layer. Preferably, such indicia take the form of regularly spaced stripes extending generally perpendicular to the longitudinal axis of the vascular patch and thereby serve as suture guidelines for aiding a surgeon in the proper and consistent placement of sutures used to secure the vascular patch to a blood vessel.

The present invention also relates to a method of forming such a vascular patch. In this regard, an expanded porous PTFE tube having inner and outer cylindrical walls is preferably selected as the starting material. A liquified elastomer is coated upon the outer cylindrical wall of the PTFE tube, but not upon the inner cylindrical wall thereof. As used herein, the term liquified elastomer should be understood to refer to an elastomer dissolved in a liquid solvent. The PTFE tube is then cut along its length to provide a relatively flat sheet from which one or more vascular patches may be cut.

As mentioned above, the vascular patch of the present invention preferably includes a colorant within the elastomeric coating. In carrying out the method of the present invention, a colorant is preferably added to the liquified elastomer before the elastomeric coating is formed upon the outer cylindrical wall of the PTFE tube.

As mentioned above, the vascular patch of the present invention preferably includes a plurality of spaced lines or stripes running generally perpendicular to the longitudinal axis of the vascular patch to serve as suture guidelines. Accordingly, in practicing the method of the present invention, stripes of PTFE ink are applied upon the outer surface of the cylindrical wall of the PTFE tube prior to the step of coating the outer wall of the tube with the liquified elastomer, with the stripes running generally perpendicular to the central axis of the PTFE tube. The preferred method of forming such stripes is to mount the PTFE tube upon a mandrel, and to rotate the mandrel at a continuous rotational speed, while moving a PTFE ink pen linearly along the outer cylindrical wall of the PTFE tube generally parallel to the central axis of the PTFE tube at a continuous rate to form a continuous helical stripe upon the outer cylindrical wall of the PTFE tube prior to applying the liquified elastomer thereto. A sintering operation bonds the PTFE ink to the outer cylindrical wall of the PTFE tube.

The liquified elastomer may be applied to the outer cylindrical wall of the PTFE tube by any technique which assures uniform distribution and controlled thickness of the resulting elastomeric coating. Preferred techniques for applying the liquified elastomer to the outer cylindrical wall of the PTFE tube include mounting the PTFE tube upon a mandrel and either dipping the mandrel in a container of the liquified elastomer, or rotating the mandrel while moving a spray nozzle along the length of the PTFE tube.

DESCRIPTION OF THE PREFERRED EMBODIMENTS

Figures 1, 2, 6, 7, 8A, 8B, 8C:
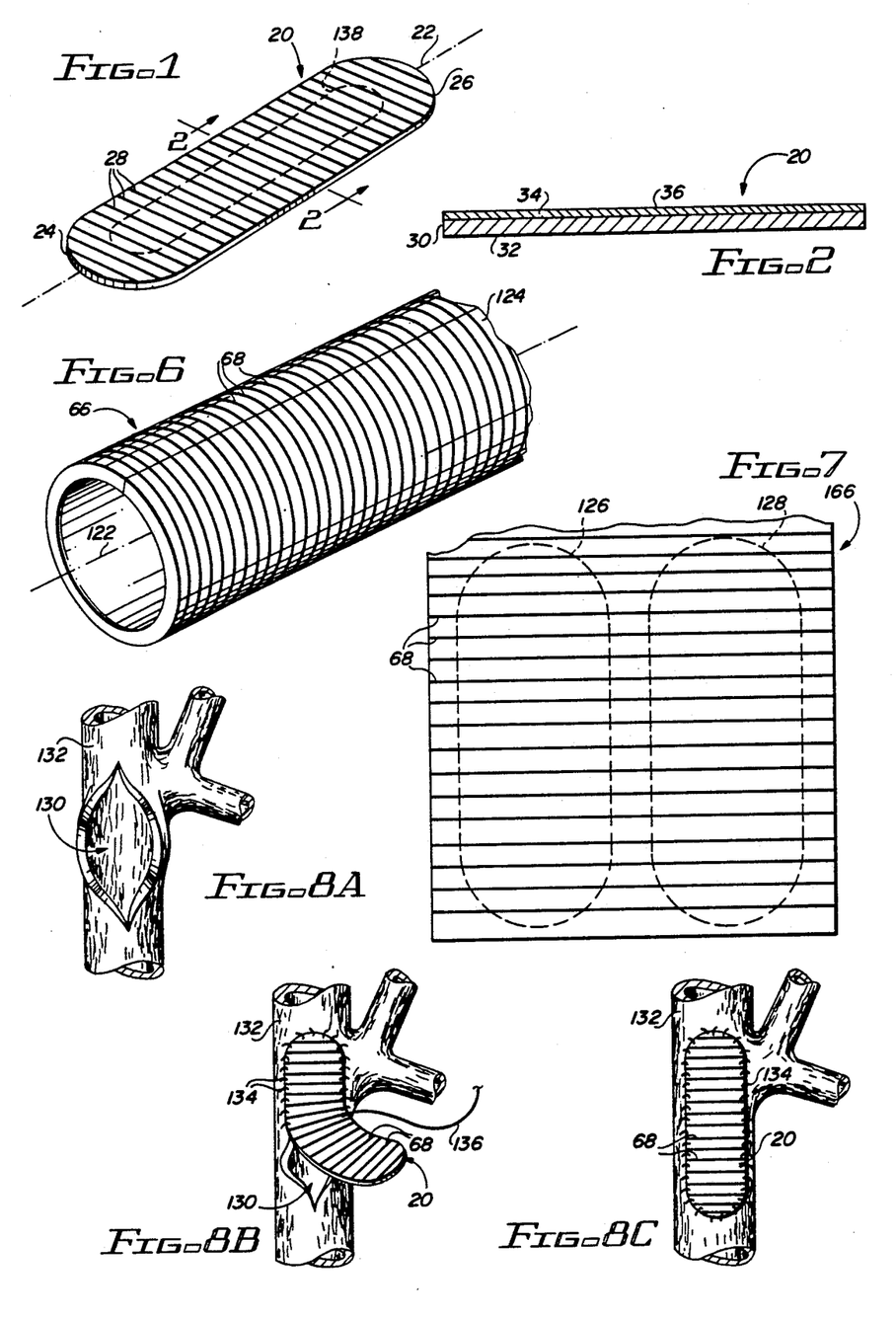
FIG. 1 is a perspective view of a blood vessel patch, or vascular patch, produced in accordance with the present invention.
FIG. 2 is a cross section of the vascular patch shown in FIG. 1 taken through the lines designated 2—2 within FIG. 1.
FIG. 6 is a perspective view of a PTFE tube having an elastomeric coating and a helical PTFE ink stripe therebeneath, and illustrates the manner in which the resulting structure is cut to form a planar sheet.
FIG. 7 is a top view of a portion of the planar sheet formed by cutting the coated PTFE tube shown in FIG. 6, and illustrating the manner in which vascular patches may be cut from the planar sheet.
FIG 8A is a top view of a carotid artery in which an incision has been formed to perform a carotid endarterectomy.
FIG. 8B is a top view similar to that shown in FIG. 8A but wherein the vascular patch of the present invention has been partially sutured to the carotid artery.
FIG 8C is a top view similar to those shown in FIG. 8A and 8B, but wherein suturing of the vascular patch has been completed.

A vascular patch produced in accordance with the teachings of the present invention is shown in FIG. 1 and is designated generally by reference numeral 20. As shown in FIG. 1, vascular patch 20 is an elongated planar strip which extends along a longitudinal axis designated by reference numeral 22. Vascular patch 20 has a first rounded end portion 24 and an opposing second rounded end portion 26. Visible within FIG. 1 are a plurality of suture guidelines 28. Suture guidelines 28 extend generally parallel to one another and generally perpendicular to the longitudinal axis 22 of vascular patch 20. Preferably, suture guidelines 28 are uniformly spaced from one another. Vascular patch 20 may be produced in sizes ranging between 3 millimeters×20 millimeters, to 50 millimeters×100 millimeters. Larger sized patches may be produced in rectangular form to allow the surgeon to customize the size and configuration of the patch as necessary at the time of prosthesis implantation.

Vascular patch 20 is shown in cross section in FIG. 2. Vascular patch 20 includes a lowermost layer 30 formed of expanded, porous PTFE material. PTFE layer 30 includes a first lumenal side 32 adapted to face and overlie a blood vessel. PTFE layer 30 also includes a second opposing ablumenal side 34 upon which an elastomeric coating 36 is formed.

The preferred starting material used to form PTFE layer 30 is expanded porous PTFE material of the type generally described within U.S. Pat. No. 4,187,390 to Gore. Such expanded, porous PTFE material is commonly used to form prosthetic vascular grafts. The preferred thickness of PTFE layer 30 ranges from 0.1 millimeter to 1.0 millimeters; the preferred internodal distance within such expanded PTFE material ranges from 10 micrometers to 60 micrometers. The longitudinal tensile strength of such PTFE material is preferably equal to or greater than 1500 Psi. When such PTFE material is configured in tubular form, the radial tensile strength of such PTFE material is preferably equal to or greater than 400 psi. The suture retention strength of such PTFE material is preferably equal to or greater than 300 grams.

In regard to elastomeric coating 36 shown in FIG. 2, such elastomeric coating is selected to be a biocompatible elastomer and may be selected from the group consisting of medical-grade silicone rubber elastomers, segmented polyurethanes, polyurethane-ureas, and silicone-polyurethane copolymers. Suitable candidates for use as elastomeric coating 36 typically have a hardness rating between 50A–100A and 55D–60D. Most of the above-mentioned elastomers can be chemically or biologically modified to improve biocompatability; such modified compounds are also candidates for use in forming elastomeric coating 36 shown in FIG. 2.

Apart from biocompatability, other requirements of an elastomer to be a suitable candidate for use as elastomeric coating 36 are that the elastomer be sufficiently elastic to effect instantaneous closure of suture holes formed by a suture needle. Elasticity should be balanced against the thickness of elastomeric coating 36, the objective being to select the minimum coating thickness necessary to prevent significant blood leakage through the suture hole locations without significantly impeding suture needle penetration. Yet another requirement of such elastomers is that they be easily dissolvable in low boiling point organic solvents such as tetrahydrofuran, methylene chloride, trichloromethane, dioxane, and dimethylformamide, by way of example. Finally, suitable elastomers should lend themselves to application to the PTFE layer 30 by either the dip coating or spray coating methods described in greater detail below.

The presently preferred elastomer used to form elastomeric coating 36 is a polyurethane formulation grade SG-80 sold under the trademark "TECOFLEX" by Thermedics, Inc. of Woburn, Mass. Such formulations are considered medical grade aliphatic polyurethanes resins of solution processible grades. Such formulations are designed to be dissolved in various solvents for use in solution casting or for coating of medical products. The polyurethane formulation is preferably dissolved in the solvent known as Tetrahydrofuran (THF), a solvent commercially available from Mallinckrodt, Inc. through the Scientific Products Division of Baxter Corp., of Irvine, California.

Further details concerning the preferred construction of vascular patch 20 shown in FIGS. 1 and 2 can more readily be understood in conjunction with the preferred method by which vascular patch 20 is produced. It has already been noted above that PTFE layer 30 is formed of expanded, porous PTFE material of a type often used to form vascular prostheses. In practicing the preferred method, the PTFE starting material is initially in the form of a cylindrical tube having an inside diameter ranging from 1.0 millimeters to 30 millimeters, and ranging in length up to 100 centimeters. The inner cylindrical wall of the PTFE tube ultimately provides the lumenal side 32 of vascular patch 20, while the outer cylindrical wall of the starting PTFE tube ultimately provides the ablumenal side 34 of PTFE layer.

As mentioned above, vascular patch 20 preferably includes suture guidelines 28 visible from the ablumenal side thereof. These suture guidelines not only help to identify the ablumenal side of the vascular patch but also assist a surgeon in properly and consistently placing the sutures used to secure vascular patch 20 to the blood vessel. The manner of forming such suture guidelines is described below in conjunction with FIG. 3.

Figure 3:
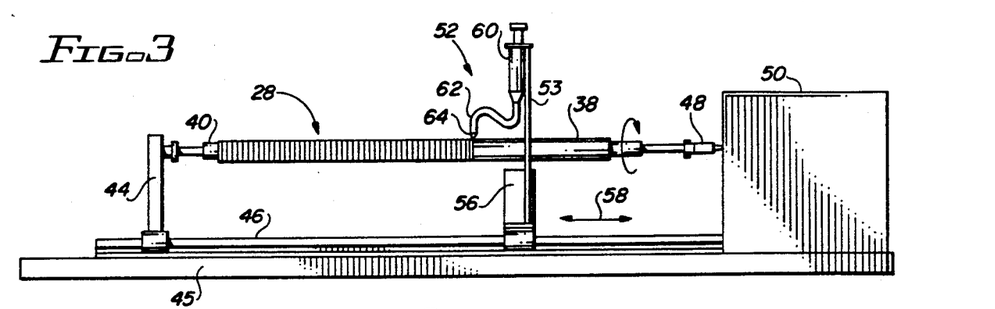
FIG 3 is a front view of a striping machine for applying a continuous helical stripe of PTFE ink to the outer cylindrical wall of a PTFE tube.

Within FIG. 3, a striping machine 42 is shown for forming the aforementioned suture guidelines. A PTFE tube 38 is shown mounted upon a rotatable mandrel 40. The outer diameter of mandrel 40 is commensurate with the inner diameter of PTFE tube 38. Mandrel 40 is rotatably supported at a first end of striping machine 42 by a support bracket 44. The lower end of support bracket 44 is secured to base 45. Also shown in FIG. 3 is a rotatable drive rod 46 which is threaded along the majority of its length but which is smooth along the portion thereof which extends through support bracket 44. The opposite end of mandrel 40 is releasably secured to a drive shaft coupling 48 extending from motor housing 50. A first motor (not shown) within motor housing 50 selectively rotates drive shaft coupling 48, and hence mandrel 40, at a uniform rotational speed for rotating PTFE tube 38. A PTFE ink pen assembly 52 is supported by a movable stand 54 for linear movement along the longitudinal axis of mandrel 40. Stand 54 is supported at its lower end by a carriage 56 which includes a threaded fitting (not shown) with which rotatable threaded drive 46 is engaged. Motor housing 50 includes a second horizontal drive motor (not shown) which rotates threaded drive rod 46 at a selectively adjustable uniform rate. Carriage 56 threadedly engages threaded rod 46 and moves linearly upon base 45 in the directions shown by dual-headed arrow 58, depending upon the direction of rotation of threaded rod 46.

The striping ink is preferably a water-based PTFE dispersion (TFE series) commercially available in several colors from Formulabs, Inc. of Piqua, Ohio. The PTFE ink is diluted to the desired viscosity in accordance with the instructions and procedures provided by the manufacturer. The striping ink is fed by gravity from reservoir 60 through plastic tube 62 to dispensing tip 64 positioned immediately above mandrel 40.

As shown in FIG. 3, a plurality of suture guidelines 28, in the form of a continuous helical stripe, is formed upon the outer cylindrical wall of PTFE tube 38 as PTFE ink pen 52 moves linearly across the upper portion of mandrel 40. The striping pattern applied to PTFE tube 38 may be varied in accordance with the rotational speed of mandrel 40 and the horizontal speed of striping pen 52. The preferred horizontal speed of striping pen 52 is 35–40 centimeters per minute, but may range up to 200 centimeters per minute depending upon the line spacing. The preferred rotational speed of mandrel 40 is 300–400 rotations per minute, but may vary up to 1000 rotations per minute. The aforementioned rotational speed and horizontal speed must be adjusted in accordance with the diameter of the PTFE tube and desired stripe width spacing. The preferred suture guideline width is 0.25–0.3 millimeters, but may range up to three millimeters depending upon intended use. Preferred line spacing is in the range of 1.2–1.5 millimeters, but may vary up to 5 millimeters.

After the striping operation shown in FIG. 3 is completed, and while PTFE tube 38 remains on mandrel 40, striped PTFE tube 38 is loaded onto a sintering rack and is heated at a temperature between 330° C. and 400° C. for 10–100 seconds in a sintering oven (not shown). The specific temperature and heating period depend upon the dimensions of the PTFE tube. The sintering operation permanently bonds the PTFE ink to the PTFE tube 38. Mandrel 40 is then removed from the sintering oven and allowed to cool to room temperature before PTFE tube 38 is removed therefrom for further processing.

Following the aforementioned sintering process, the above-described elastomeric coating may then be applied to the outer cylindrical wall of PTFE tube 38. As mentioned above, the two preferred methods of applying the elastomeric coating are dip coating and spraying. Regardless of which application method is used, the preferred method of formulating the liquified elastomer is the same. As has been described, the preferred liquified elastomer is formed by preparing a solution of "Tecoflex" polyurethane grade SG-80A. This solution is prepared by dissolving polyurethane pellets in the above-described terahydrofuran solvent in a heated glass reactor equipped with a cold water condenser held at 60° C. Such polyurethane pellets may also be dissolved in the solvent at room temperature through continuous stirring. The use of the heated reactor is preferred, as it dissolves the polyurethane pellets in a few hours, whereas the method of stirring the solution at room temperature takes approximately two days.

The preferred solids contents for "Tecoflex" grade SG-80A is 2–4 percent by weight; however, the solids content may range up to 15 percent by weight, depending upon the specific polymer composition, the dip coating parameters, and the intended end uses. Where multiple coatings are employed, the composition of the polyurethane solution may be varied between coating layers. For example, it might be advantageous to apply progressively more dilute polyurethane solutions to the underlying PTFE tube.

It will be recalled that the incorporation of a colorant within the elastomeric coating may be desired to more readily identify the ablumenal side of the completed vascular patch. The colorant may be added directly to the above-described polyurethane solution. The preferred colorant is Meteor Cobalt Blue, manufactured by Engelhard Harshaw Company of Cleveland, Ohio, under product No. 7540. The manufacturer designates such product as Cobalt Aluminate Blue Spinel, with a color index number of CI 77346, a color index name of CI Blue 28, and a Chemical Abstracts Service Registry number of 68186-86-7. While such colorant has not been labelled as a medical grade material by the manufacturer, this colorant has been previously approved by the U.S. Food and Drug Administration for use in conjunction with other implantable prosthetic devices. As mentioned above, when multiple coatings are applied to the PTFE tube, the composition of the polyurethane solution may be varied between coatings. For example, it may be desirable to add a colorant only to the first several layers of the coating. Furthermore, while Cobalt Blue is preferred as a colorant, other colorants meeting FDA color additive guidelines may also be used.

Yet another method of adding a colorant to the outer cylindrical wall of the PTFE tube is to add a colorant to the PTFE resin itself during the process of extruding the PTFE tube. To make a PTFE tube with a colored outer wall, a special barrel is used to form the billet of the PTFE resin. A spacer tube within the billet divides the barrel into an inner ring and an outer ring. A colorant is added to the resin that is provided in the outer ring, while conventional uncolored resin is provided within the inner ring. When this billet is extruded using conventional PTFE extrusion techniques, the resultant PTFE tubes perform normally but have a colored outer layer on the ablumenal surface.

Following preparation of the liquified polyurethane solution as described above (with or without a colorant), the next step is to apply the polyurethane solution as a coating upon the outer wall of the PTFE tube. The method of dip coating the PTFE tube will now be described in conjunction with FIG. 4, which illustrates a dip coating machine.

Figure 4:
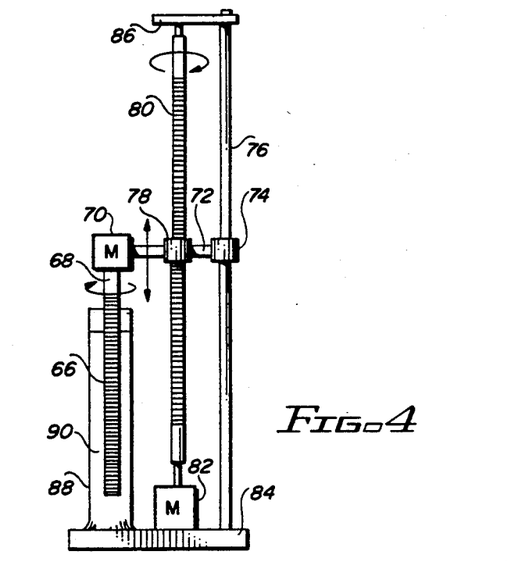
FIG. 4 is a front view of a dip coating apparatus adapted to apply a uniform elastomeric coating to the outer cylindrical wall of a PTFE tube.

FIG. 4 illustrates a dip coating machine designated generally by reference numeral 65. To perform the dip coating procedure, the striped PTFE tube 38, as shown in FIG. 3, is removed from mandrel 40 and is preferably cut to form two or three PTFE tubes of shorter length, each approximately 25 centimeters long. One of such 25 centimeter long PTFE tube sections, designated by reference numeral 66 in FIG. 4, is stretched over a second mandrel 68. Preferably, mandrel 68 is selected to have a diameter that is approximately 0.2–0.4 millimeters larger than the inside diameter of PTFE tube section 66 to prevent PTFE tube section 66 from sliding upon mandrel 68 during the coating process. Mandrel 68 is approximately 25–30 centimeters long. Lengths in excess of 30 centimeters are not preferred due to the effects of gravity pulling upon the polyurethane coating during the coating process; attempts to process PTFE tube sections much in excess of 25-30 centimeters in length can result in uneven coating thicknesses as measured between the top and bottom of mandrel 68.

As shown in FIG. 4, mandrel 68 extends vertically downward from a motor 70 which continuously rotates mandrel 68 and PTFE tube section 66 secured thereto. Motor 70 is, in turn, supported by a bracket 72 adapted to travel vertically upward and downward. Bracket 72 includes a smooth bushing 74 through which a smooth vertical support rod 76 passes. Bushing 74 is adapted to slide upwardly and downwardly along support rod 76. Bracket 72 further includes a threaded collar 78 through which a threaded rotatable drive rod 80 passes. The lowermost end of drive rod 80 is secured to the drive shaft of a second motor 82 which rotates in a first rotational direction to raise mandrel 68 and which rotates in an opposing rotational direction to lower mandrel 68. Both motor 82 and support rod 76 are supported at their lower ends by a base 84. The upper end of support rod 76 is fixedly secured to bracket 86 which rotatably supports the upper end of drive rod 80. Motor 82 of dip coating machine 65 is initially operated to raise mandrel 68 to its uppermost position. A tall, slender container 88 containing the above-described polyurethane solution 90 is placed upon base 84 immediately below mandrel 68. Motor 82 may then be operated in the reverse rotational direction to lower mandrel 68, and PTFE tube section 66 secured thereto, into polyurethane solution 90.

The variables controlled by dip coating machine 65 include the speed at which mandrel 68 is immersed and withdrawn, the rotational speed of mandrel 68, and the drying time between successive coatings. These parameters are controlled to ensure that the polymer coating penetration is restricted to the outer layers of the PTFE tube section 66.

The preferred number of polyurethane solution coatings applied to PTFE tube section 66 is eight, but may range between one and twenty coatings, depending upon the concentration of the elastomer solution used in the dipping process, and depending upon the intended use of the end product. The preferred coating thickness at the completion of the dip coating process is between 0.06-0.08 millimeters, but may vary up to two millimeters, depending upon the dimensions of the coated tube and the elastomer solution concentration.

The dip coating procedure of immersing and then withdrawing PTFE tube section 66 is a continuous process, and PTFE tube section 66 is continuously in motion at any given time during the procedure. Drying intervals between successive polyurethane coatings can vary up to a few hours depending upon the type of solvent used and the drying conditions. PTFE tube section 66 is dried in ambient air, preferably in an inert atmosphere, but may also be dried at elevated temperatures of 40-100° C. PTFE tube section 66 remains secured to mandrel 68 until the coating and drying process described above is completed. When the last of 60 micrometers. The longitudinal tensile strength of such PTFE the eight coatings has substantially dried, PTFE tube section 66 is further dried under vacuum at 50° C. at 10-15 mmHg vacuum for 10-24 hours to completely remove any remaining solvents. The polyurethane coated PTFE tube is then ready for being cut into vascular patches in the manner described below.

A second method for applying the polyurethane coating to the striped PTFE tube involves the use of spraying and will now be described in conjunction with the spray coating machine shown in FIG. 5. The polyurethane solution to be sprayed is first prepared in the same manner as described above for the dip coating process. The polyurethane solution is inserted within cylinder 92 of a pump 94 for delivery through a plastic tube 96 to a spray nozzle 98. An inert gas, such as nitrogen, is also supplied to spray nozzle 98 through connecting tube 100 from supply tank 102. An inert gas is preferably used to minimize reactions which polyurethane can undergo upon exposure to air and oxygen.

Figure 5:
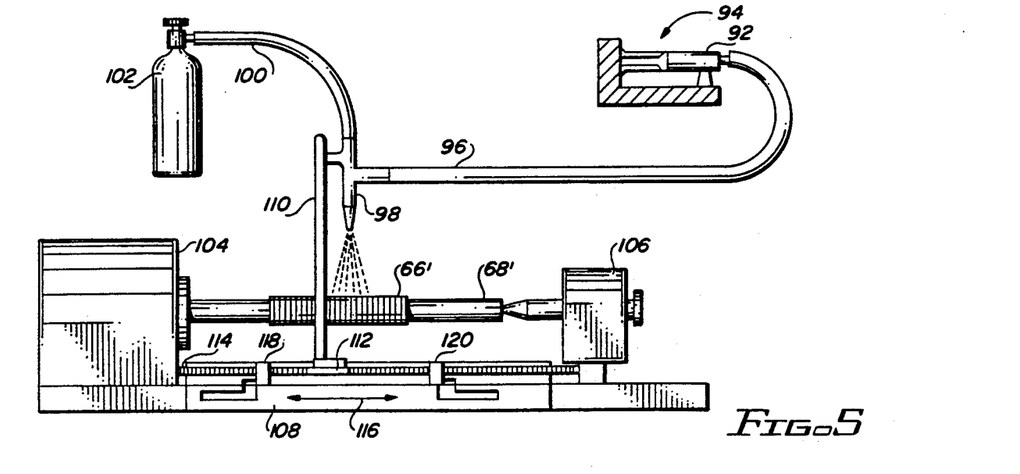
FIG. 5 is a front view of an apparatus which may be used to spray a liquified elastomer upon the outer cylindrical wall of a PTFE tube to form a uniform elastomeric coating thereupon.

Still referring to FIG. 5, PTFE tube section 66' is again stretched over a mandrel 68'. Once again, mandrel 68' is preferably of a slightly larger diameter slightly larger than the inner diameter of PTFE tube section 66' to prevent PTFE tube section 66' from sliding thereupon. Mandrel 68' is supported for rotation about a horizontal axis. One end of mandrel 68' is coupled to the drive shaft of a first motor (not shown) within motor housing 104, while the opposite end of mandrel 68 is rotatably supported by bracket 106. Both motor housing 104 and bracket 106 are supported upon base 108. The aforementioned first motor continuously rotates mandrel 68' at speeds of up to 500 rotations per minute.

Spray nozzle 98 is supported for reciprocal movement above and along mandrel 68'. As shown in FIG. 5, spray nozzle 98 is secured to support rod 110 which includes at its lowermost end a carriage 112. A threaded drive rod 114 is coupled at a first end to the drive shaft of a second motor (not shown) within motor housing 104 for being rotated thereby. The opposite end of threaded drive rod 114 is supported by and freely rotates within bracket 106. Threaded drive rod 114 threadedly engages a threaded collar (not shown) within carriage 112. Accordingly, rotation of drive rod 114 causes carriage 112, and hence spray nozzle 98, to move in the directions designated by dual headed arrow 116, depending upon the direction of rotation of drive rod 114. Also shown in FIG. 5 are a pair of microswitches 118 and 120 which are periodically engaged by carriage 112 and which, when actuated, reverse the direction of rotation of threaded drive rod 114 in a manner which causes spray nozzle 98 to reciprocate back and forth along mandrel 68'.

As shown in FIG. 5, spray nozzle 98 makes several passes along mandrel 68', repetitively spraying PTFE tube section 66' as it rotates. Spray nozzle 98 is caused to travel at a linear speed of up to 50 centimeters per minute. The polyurethane coating thickness which results from this spraying process is determined by the speed of rotation of mandrel 68', the linear speed of spray nozzle 98, the concentration of the polyurethane solution, as well as the rates of delivery of both the polyurethane solution by pump 94 and the rate of delivery of inert gas. These rates of delivery may range up to 5 milliliters per minute for the polyurethane solution, and up to 5 liters per minute for the nitrogen gas. After an appropriate number of spray cycles, the PTFE tube is vacuum dried in the manner described above and slipped off of mandrel 68'.

After the coating and drying processes described above are completed, the resulting polyurethane-coated PTFE tube has the appearance generally shown in FIG. 6. Within FIG. 6, the longitudinal axis of PTFE tube 66 is designated by dashed line 122. To form a planar sheet of the coated PTFE material, PTFE tube 66 is cut open, as along the cut line 124 shown in FIG. 6. Cut line 124 is made generally parallel to central axis 122 and generally perpendicular to the suture guideline 68. The aforementioned cut may be made using a sharp razor blade or scissors. A smaller diameter mandrel (not shown) may be inserted within coated PTFE tube 66 to support the same during the cutting procedure.

After being cut open, coated PTFE tube 66 is laid open and gently stretched in the circumferential direction until it forms a flat sheet 166, as shown in FIG. 7. Vascular patches of desired size, such as those indicated by dashed lines 126 and 128 within FIG. 7, may then be cut or stamped out of flat sheet 166 by using appropriately sized cutting dies. The stamped vascular patches may then be individually packaged in double sterile configuration, and may be sold individually or in sets. Vascular patches 126 and 128 are oriented so that their longitudinal axes extend generally perpendicular to the suture guidelines 68. Referring now to FIGS. 8A–8C, the manner in which vascular patch 20 of FIG. 1 is used will be briefly described below. In FIG. 8A, an incision 130 is shown as having been made within a carotid artery 132 at an endarterectomy site. Such an incision might be made within the carotid artery to facilitate removal of atherosclerotic plaque by endarterectomy. In FIG. 8B, vascular patch 20 of FIG. 1 is shown partially sutured around incision 130 to close the incision. Within FIG. 8B, a typical suture attachment is designated by reference numeral 134, while the free end of the suture material is designated by reference numeral 136.

In FIG. 8C, suturing of vascular patch 20 is completed, and incision 130 is completely closed. Within FIGS. 8B and 8C it will be noted that suture guidelines 68 provide a convenient means for uniformly spacing sutures 134 along the periphery of vascular patch 120.

Returning to FIG. 1, a dashed oval 138 is indicated on vascular patch 20. Those skilled in the art will appreciate that only the peripheral portions of vascular patch 20 lying outside dashed oval 138 need receive the elastomeric coating to minimize suture hole bleeding, since the sutures penetrate vascular patch 20 only in such peripheral region. Nonetheless, in view of the above-described method of producing such vascular patches, it is typically easier to coat the entire ablumenal surface of vascular Patch 20 with the elastomeric coating.

A prototype vascular patch produced in accordance with the method described herein was implanted in a dog, and practically no bleeding was observed at the suture holes. In addition, a laboratory simulation was conducted in a manner described below to determine the susceptibility of such vascular patches to suture hole bleeding. Test segments were taken from two PTFE tube sections, each measuring 19 millimeters in internal diameter, one of such tube sections being pure PTFE having a wall thickness of 0.774 millimeters and the second PTFE tube section having a wall thickness of 0.594 millimeters and having a polyurethane coating thickness of 0.088 millimeters applied to it in the manner described above. A two inch length from each of the aforementioned tube sections was clamped between two hemostats, and ten 6-0 polypropylene sutures were placed in a continuous fashion in the middle of each tube. The test sections were then each pressurized to 2 psi with water, and water loss through the suture holes was measured for a one minute period. Similar measurements were also made with the water pressure being raised to 4 psi. Leak rate measurements obtained by the procedure described above are set forth below.

| Water Pressure (Psi) | Non-coated PTFE Tube | Leak Rate (ml/min) Coated PTFE Tube |
|---|---|---|
| 2 psi | 11.04 | 3.44 |
| 4 psi | 19.96 | 8.3 |

By way of comparison, normal blood pressures within the human body typically range from 1.8 to 2.3 psi.

Those skilled in the art will now appreciate that an improved vascular patch has been described which provides all of the advantages of prosthetic PTFE patches while minimizing suture hole bleeding. While the invention has been described with reference to a preferred embodiment thereof, the description is for illustrative purposes only and is not to be construed as limiting the scope of the invention. Various modifications and changes may be made by those skilled in the art without departing from the true spirit and scope of the invention as defined by the appended claims.

We claim:

1. A vascular patch for patching incisions in blood vessels, comprising in combination:
    a. a substantially planar layer of expanded PTFE having a first lumenal side for overlying a blood vessel and having a second opposing ablumenal side for facing away from the blood vessel; and
    b. a non-porous elastomeric coating applied over at least the peripheral portions of the ablumenal side of the expanded PTFE layer to minimize suture hole bleeding resulting from the application of sutures to the vascular patch.

2. A vascular patch as recited by claim 1 wherein said elastomeric coating is applied over the entire ablumenal side of the expanded PTFE layer but not over the lumenal side of the expanded PTFE layer.

3. A vascular patch as recited by claim 1 wherein said elastomeric coating is a layer of polyurethane.

4. A vascular patch as recited by claim 3 wherein said polyurethane layer has a colorant therein to distinguish the uncoated lumenal side of the expanded PTFE layer from the coated ablumenal side of the expanded PTFE layer.

5. A vascular patch for patching incisions in blood vessels, comprising in combination:
    a. a layer of expanded PTFE having a first lumenal side for overlying a blood vessel and having a second opposing ablumenal side for facing away from the blood vessel; and
    b. a layer of polyurethane coated over the ablumenal side of the expanded PTFE layer but not over the lumenal side of the expanded PTFE layer, said polyurethane layer having a colorant therein to distinguish the uncoated lumenal side of the expanded PTFE layer from the coated ablumenal side of the expanded PTFE layer.

6. A vascular patch for patching incisions in blood vessels, comprising in combination:
    a. a layer of expanded PTFE having a first lumenal side for overlying a blood vessel and having a second opposing ablumenal side for facing away from the blood vessel;
    b. indicia formed upon the ablumenal side of the PTFE layer;
    c. a layer of an elastomer coated over the ablumenal side of the expanded PTFE layer;

d. said indicia being visible through the layer of elastomer to distinguish the uncoated lumenal side of the expanded PTFE layer from the coated ablumenal side of the expanded PTFE layer.

7. A vascular patch as recited by claim 4 wherein said indicia is comprised of PTFE ink.

8. A vascular patch as recited by claim 4 wherein said indicia includes suture guidelines for aiding a surgeon in the proper and consistent placement of sutures used to secure the patch to a blood vessel.

9. A vascular patch as recited by claim 6 wherein said elastomer is selected from the group of elastomers consisting of medical-grade silicone rubber elastomers, segmented polyurethane, polyurethane-ureas, and silicone-polyurethane copolymers.

10. A vascular patch as recited by claim 6 wherein said elastomer has a hardness rating between 50A–100A and 55D–60.

11. A vascular patch for patching incisions in blood vessels, comprising in combination:
  a. a substantially planer layer of expanded PTFE having a first lumenal side for overlying a blood vessel and having a second opposing ablumenal side for facing away from the blood vessel;
  b. a non-porous layer of an elastomer coated over the ablumenal side of the expanded PTFE layer, said layer of elastomer being substantially transparent; and
  c. said layer of expanded PTFE including a colorant proximate one of the lumenal or ablumenal sides thereof, said colorant distinguishing the uncoated lumenal side of the expanded PTFE layer from the coated ablumenal side of the expanded PTFE layer.

* * * * *